United States Patent [19]

Kebabian

[11] Patent Number: 5,291,265
[45] Date of Patent: Mar. 1, 1994

[54] OFF-AXIS CAVITY ABSORPTION CELL

[75] Inventor: Paul L. Kebabian, Acton, Mass.

[73] Assignee: Aerodyne Research, Inc., Billerica, Mass.

[21] Appl. No.: 893,120

[22] Filed: Jun. 3, 1992

[51] Int. Cl.⁵ .................... G01N 21/05; G01N 21/35
[52] U.S. Cl. ................................. 356/246; 250/343; 356/440
[58] Field of Search ............ 356/246, 440, 437; 250/343; 372/107

[56] References Cited

U.S. PATENT DOCUMENTS

| | | |
|---|---|---|
| 3,253,226 | 5/1966 | Herriott et al. . |
| 3,437,954 | 4/1969 | Herriott et al. . |
| 3,550,039 | 12/1970 | Herriott . |
| 5,002,391 | 3/1991 | Wolfrum et al. ............... 356/437 X |
| 5,121,405 | 6/1992 | Negus .............................. 372/107 |

OTHER PUBLICATIONS

John U. White, "Long Optical Paths of Large Aperture," *J. Opt. Soc. Am.*, May 1942.
Herriott et al., "Off-Axis Paths in Spherical Mirror Interferometers," *Applied Optics*, Apr. 1964.
Herriott et al., "Folded Optical Delay Lines," *Applied Optics* Aug. 1965.
Kogelnik et al., "Laser Beams and Resonators," *Applied Optics* Oct. 1966.
McManus et al., "Narrow Optical Interference Fringes for Certain Setup Conditions in Multipass Absorption Cells of the Herriott Type," *Applied Optics*, Mar. 1, 1990.

*Primary Examiner*—Vincent P. McGraw
*Attorney, Agent, or Firm*—Cesari and McKenna

[57] ABSTRACT

An off-axis cavity absorption cell (10) includes astigmatic mirrors (22, 28). The cell design is based on a prototype design that yields a closed beam path having a desired geometry, but the mirrors are fabricated so that the ratios of their radii of curvature are actually larger than those calculated for the prototype. To achieve the desired closed beam path, the mirror spacing is adjusted from that of the prototype design, and the planes of their axes of greatest curvature are oriented out of the alignment that characterizes the prototype design. If the mirrors' manufacturing process yields errors in the curvature-radius ratios within certain prescribed limits, a cell of this design can be adjusted to achieve the closed beam path by simply changing the mirror separation and the "twist angle" between their respective planes of maximum curvature radius.

11 Claims, 5 Drawing Sheets

OFF-AXIS CAVITY ABSORPTION CELL

This invention was made with government support under Grant No. ISI-8907681 awarded by the National Science Foundation. The government has certain rights in this invention.

BACKGROUND OF THE INVENTION

The present invention is directed to absorption cells. It particularly concerns off-axis cavity absorption cells.

In order to detect trace atmospheric chemical constituents in a gas sample by, for instance, infrared-absorption spectroscopy, the need to obtain measurable absorption often requires that a beam of light propagate a relatively long distance through the sample. To obtain this effect in a small space, a beam is often caused to reflect repeatedly between opposed mirrors.

Typically, an absorption cell is an elongated cylinder in which the mirrors are disposed at opposite ends, and light is coupled into and out of the cell through one or more holes in the mirrors, although some equivalent approach, such as the use of a small internal mirror, can also be employed.

A key factor that determines the cell's cross-sectional area, and thus its volume, is that the light beam should remain clear of the exit aperture before it has traversed the desired distance inside the cell. The spots at which the beam lands on each mirror always have a certain minimum size, which is imposed by the wave nature of light in the case of coherent light, such as that from a laser, or by the need to transmit a measurable flux from the source to the detector in the case of an incoherent source, such as a heated body. Given this constraint, the pattern that successive spots make on a mirror in a given configuration determines the cell size.

In the configuration described by J. White, "Long Optical Paths of Large Aperture," *J. Opt. Soc. Am.* vol. 32, pages 285-288 (1942), for instance, the spots occur in a single row. Most later implementations of that concept produce two parallel rows of spots, while the configuration described in Herriott et al., "Off-Axis Paths in Spherical Mirror Interferometers," *Applied Optics* vol. 3, pages 523-526 (1964), produces a circular or elliptical pattern. In all of these arrangements, the cell width increases relatively rapidly with the number of traverses that the beam makes of the cell's base length.

Herriott et al., "Folded Optical Delay Lines," *Applied Optics* vol. 4, pages 883-889 (1965) ("Herriott et al. II") describes a configuration that offers an important advantage over previous designs. In that configuration, the spots are spread over the surface in the mirror in two dimensions, so the required mirror diameter increases more slowly with the number of traverses. This configuration has not enjoyed wide acceptance, however, because its fabrication is difficult and costly.

The reason for this difficulty and cost is that the Herriott et al. II arrangement employs astigmatic mirrors, and for the beam to leave the cell at a point sufficiently close to the center of the (single) coupling aperture, the ratio of the mirrors' radii of curvature must be controlled to a very high accuracy. To realize a typical cell to provide a few hundred traverses in the mid-infrared region, for instance, requires that the relative error in that ratio be less than 0.01 percent. In most cases, the difficulty and cost of fabricating an aspheric mirror to that degree of accuracy are prohibitive.

To avoid that necessity, the astigmatism provided in Herriott et al. II was achieved by mechanically warping initially spherical mirrors. To obtain the greatest benefit from the astigmatic-mirror principle, however, the mirrors must have greater astigmatism than can be achieved as a practical matter by warping a spherical mirror. Even as a way to correct the curvature of a mirror with ground-in astigmatism, moreover, mechanical warping is disadvantageous. Specifically, stress relief in the warping elements (typically, springs) or in the mirror itself results in correction drift, and the temperature coefficients of the mirror's and warping elements' elastic properties have to be closely controlled.

SUMMARY OF THE INVENTION

The present invention achieves the advantages of the Herriott et al. II astigmatic-mirror principle without stringent requirements on manufacturing tolerances or the need to impose mechanical stresses to compensate for inaccuracies in the mirrors' manufacture.

According to the present invention, compensation for errors in the mirrors' curvature-radii ratios is accomplished by adjusting the distance between the mirrors and by adjusting their twist angle, i.e., the "roll" angle between them about the axis through their centers. This approach can be employed so long as the actual curvature-radii ratio of the manufactured mirrors is at least as great as the nominal value that would result in the desired path length and exit point with zero twist angle if precisely achieved. Therefore, by manufacturing the mirrors to specifications such that this ratio will exceed the nominal value even in the worst case within known tolerance limits, the proper path can be achieved by adjusting the mirror separation and twist angle. As a practical matter, this means that an absorption cell built in accordance with teachings of the present invention will almost always have a twist angle greater than one degree and usually greater than ten degrees.

Moreover, I have found that the adjustment process is relatively easy to perform; it turns out that the component of the final spot's position in the direction in which it moves in response to a mirror-separation change is largely independent of twist angle, and vice versa.

BRIEF DESCRIPTION OF THE DRAWINGS

The foregoing and related features and advantages of the present invention are described in connection with accompanying drawings, in which.

DETAILED DESCRIPTION OF ILLUSTRATIVE EMBODIMENTS

Figure 1:
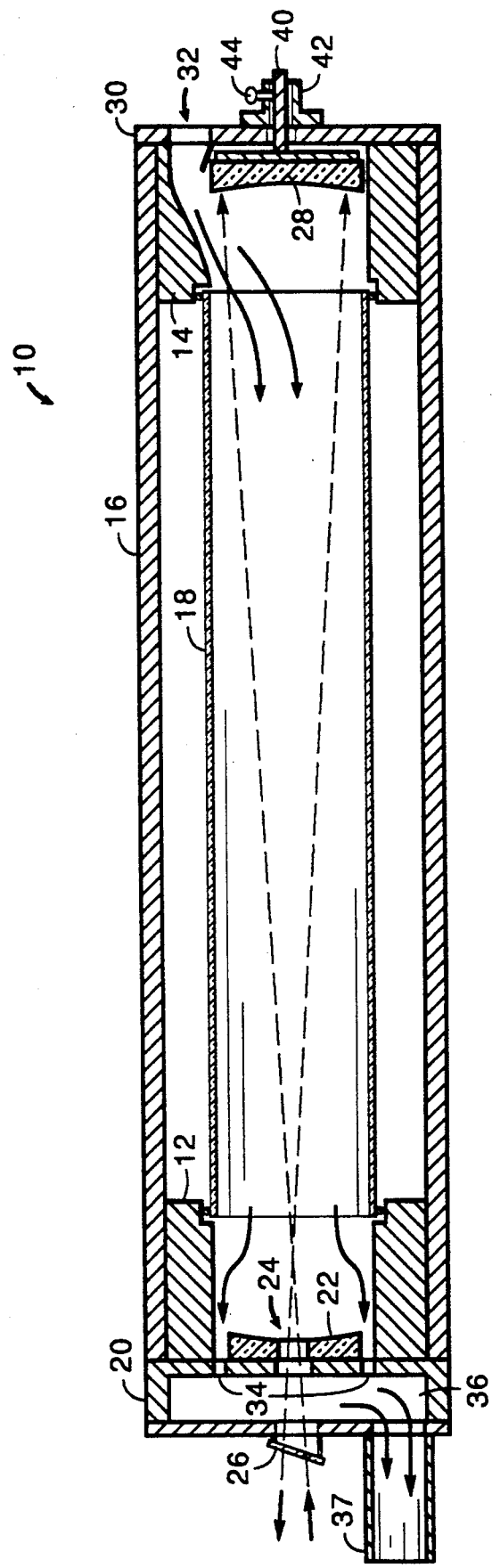
FIG. 1 is a cross-sectional view of an absorption cell of the type in which the teachings of the present invention can be applied.

FIG. 1 depicts an absorption cell 10 that, with one exception, is largely conventional in its arrangement. Generally annular filler blocks 12 and 14 are mounted at opposite ends inside a pressure vessel 16 and serve to secure a glass liner 18 that largely defines a cavity containing the gas to be analyzed.

A hollow, disk-shaped end piece 20 mounted on the front end of the pressure vessel supports an astigmatic front mirror 22 through which a coupling aperture 24 has been bored. A window 26 is provided in the front end piece 20 to permit a light beam to enter at a predetermined angle and pass through the coupling aperture 24 on its way to a rear astigmatic mirror 28 mounted on a rear end piece 30. Although nothing in principle restricts the applicability of the present invention to any particular astigmatism range so long as the cell meets the other requirements set forth below, the ratio of each mirror's greatest curvature radius to its smallest curvature radius should exceed 1.001 if any significant benefit is to be obtained from the astigmatic-mirror feature.

Through an inlet conduit 32 in the rear end piece, gas to be analyzed enters the cavity and passes from the cavity by means of ports 34 into an exhaust plenum 36 that the front end piece 20 forms. An exhaust pipe 37 may be provided in the front end. Of course, this arrangement of gas flow is merely exemplary; all that is necessary is that there be some way to admit gas into the cavity through which the light travels.

A light beam that enters at the predetermined angle is reflected back and forth between mirrors 22 and 28 a predetermined large number of times before finally leaving through the coupling aperture 24. The number of reflections that occur before the light finally leaves the cavity is, of course, a function of the specific design parameters.

Figure 2:
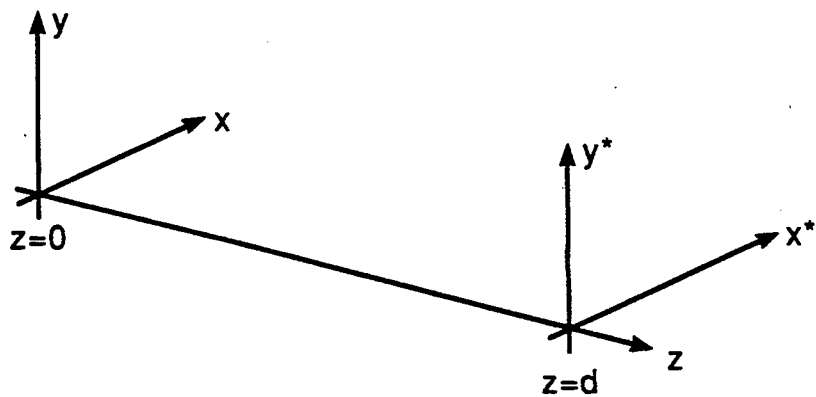
FIG. 2 is a diagram that will be used to describe the cell's mirror geometry.

Consider the coordinate system that FIG. 2 depicts. Assume that the z axis is the axis that passes through the mirrors' center and that the surface of the front mirror 22 intersects this axis at $z=0$, while the corresponding intersection of the back mirror surface occurs at $z=d$. The x and y axes are mutually orthogonal and orthogonal to the z axis in the ordinary Cartesian arrangement.

The x and y axes are the front mirror's principal axes: they are so aligned with the front mirror that the ratio of the corresponding curvature radii is maximized. That is, if $r_x$ is the radius of curvature of the front-mirror surface's intersection with the xz plane and $r_y$ is the radius of curvature of its intersection with the yz plane, then the coordinate axes are so oriented as to maximize $r_y/r_x$. Conventionally, the back mirror is so aligned with the front mirror that the same result prevails, but it will become convenient to have defined a second, $x^*y^*$ coordinate-axis pair similarly aligned with the back mirror.

If, as is conventional, the x and y axes are respectively aligned with the $x^*$ and $y^*$ axes, the coordinates of the nth return of the beam to the front mirror at $z=0$ are:

$$x_n = A \sin(n\theta_x) \text{ and}$$

$$y_n = B \sin(n\theta_y),$$

where coefficients A and B are proportional to the slope of the entering beam, and $\theta_x$ and $\theta_y$ are given by:

$$\cos \theta_x/2 = 1 - d/r_x \text{ and}$$

$$\cos \theta_y/2 = 1 - d/r_y.$$

Of course, a design requirement is that the beam leave the coupling aperture at $x=y=z=0$ after N cycles (2N traverses of the base path) but not before, and this result occurs if the mirror radii are selected such that $\theta_x = 2\pi k_x/N$ and $\theta_y = 2\pi k_y/N$, where $k_x$ and $k_y$ are integers, N is an odd integer, and the common divisors (other than 1) of $k_x$ and N are different from those of $k_y$ and N. i.e., the sequence of spots at which the light beam hits a mirror forms a Lissajous pattern that executes $k_x$ cycles in the x direction and $k_y$ cycles in the y direction in the course of 2N traverses of the base path. These relationships are the design criteria for a conventional astigmatic cell of the type described in Herriott et al. II.

A cell designed in accordance with the present invention is based on a "prototype" cell design that meets such criteria, but the actual cell differs from the prototype cell on which it is based. Specifically, the first step in making a cell in accordance with the present invention is to design an absorption cell in which the mirrors are aligned and in which the foregoing parameter relationships prevail. As was explained above, it would be quite difficult to make such a prototype cell, since the tolerances required of the curvature-radius ratio would be very tight. I have recognized, however, that adjusting the mirror separation and adding a "twist angle" between the mirrors—i.e., between the x and y axes on the one hand and the $x^*$ and $y^*$ axes on the other—can eliminate any error in the location of the Nth return to the front-mirror plane (which should occur at $x=y=0$) despite otherwise unacceptable tolerances in $r_y/r_x$ so long as the actual value of $r_y/r_x$ exceeds the prototype-cell value.

Now assume that the mirrors can be manufactured such that their curvature radii are correct to a relative tolerance of e, i.e., when prototype radii $r_x$ and $r_y$ are specified, such that $$|r_x - r_x'| < er_x \text{ and}$$

$$|r_y - r_y'| < er_y,$$

where primed and unprimed quantities are the actual and prototype values, respectively. If the "design center" values, to which the mirrors are manufactured, are given by $r_x'' = r_x(1+e)$ and $r_y'' = r_y/(1-e)$, where the double-primed values are the design-center values, we can be sure that the ratio $r_y'/r_x'$ will exceed the prototype-cell value so long as the curvature radii are within tolerances. As a practical matter, some slightly greater value $e' = e + \Delta e$ will be used to determine the design-center values so that the actual radii values always end up differing from the prototype values by a minimum amount $\Delta e$, i.e., so that $$r_x'' = r_x(1+e') \text{ and } r_y'' = r_y/(1-e');$$

i.e., the actual mirrors will end up with radius values of $r_x' < r_x(1+\Delta e)$ and $r_y' > r_y/(1-\Delta e)$. I believe that a $\Delta e$ value of $2 \times 10^{-4}$ leaves enough room for path adjustment by twist-angle and mirror-separation variation.

If thus-specified mirrors are aligned in the ordinary manner, the light will not typically return out through the center of the coupling aperture 24 after exactly N cycles through the cell as required. According to the present invention, however, the light path is adjusted to meet this requirement by adjusting both the distance between the mirrors and the twist angle between the front mirror's x and y axes and the back mirror's x* and y* axes.

Figure 3:
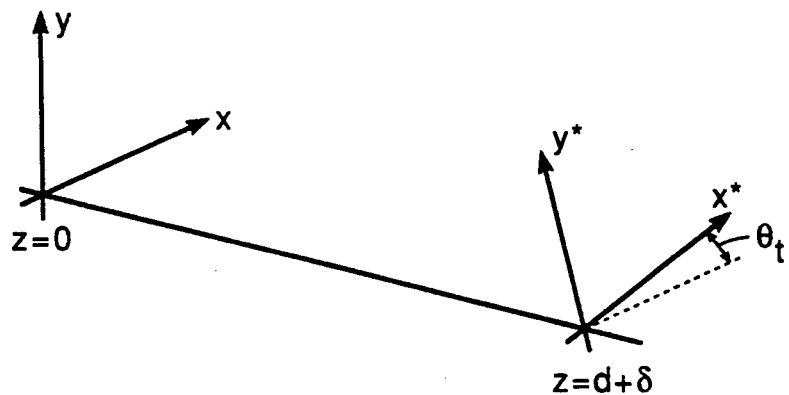
FIG. 3 is a diagram similar to FIG. 2 for describing the adjustment by which mirror manufacturing tolerances are accommodated in accordance with the present invention.

That is, instead of placing the mirrors in the positions schematically depicted in FIG. 2, the mirrors are instead positioned and oriented in accordance with a twist angle $\theta_t$ and separation offset $\delta$ defined in FIG. 3. This may be done, for instance, by mounting the back mirror 28 on a small shaft 40 that fits in a bushing 42 in which it can be translated and rotated until secured in place by a set screw 44. The separation and twist angle are then adjusted until the light beam hits the center of the exit aperture 24 at the end of N cycles.

The adjustment process can be expedited by beginning with a twist angle and separation that would result in the proper final-spot position if the manufacturing process had actually resulted in exactly the design center values.

These values of twist angle and separation can be found by, for instance, employing the ray-matrix formalism exemplified by Kogelnik et al., *Proc. IEEE* vol. 54, pp. 1312–1329 (1966). In accordance with this approach, a ray propagating along the mirror path is represented by a column vector $[x, x', y, y']^T$, where $x'$ and $y'$ are the beam's slopes in the x and y directions, respectively, and superscript T denotes transposition. In accordance with this representation, if a ray propagates a distance $d+\delta$ in the z direction from point a to point b, the column vector that represents it at point b can be computed from the vector that represents it at point a in accordance with:

$$\begin{bmatrix} x_b \\ x_b' \\ y_b \\ y_b' \end{bmatrix} = \begin{bmatrix} 1 & d+\delta & 0 & 0 \\ 0 & 1 & 0 & 0 \\ 0 & 0 & 1 & d+\delta \\ 0 & 0 & 0 & 1 \end{bmatrix} \begin{bmatrix} x_a \\ x_a' \\ y_a \\ y_a' \end{bmatrix} = D(d+\delta) \begin{bmatrix} x_a \\ x_a' \\ y_a \\ y_a' \end{bmatrix}.$$

While propagation through free space is represented by the matrix D, reflection from aligned astigmatic mirrors is represented by a matrix R:

$$\begin{bmatrix} x_b \\ x_b' \\ y_b \\ y_b' \end{bmatrix} = \begin{bmatrix} 1 & 0 & 0 & 0 \\ -1/r_x & 1 & 0 & 0 \\ 0 & 0 & 1 & 0 \\ 0 & 0 & -1/r_y & 1 \end{bmatrix} \begin{bmatrix} x_a \\ x_a' \\ y_a \\ y_a' \end{bmatrix} = R(r_x, r_y) \begin{bmatrix} x_a \\ x_a' \\ y_a \\ y_a' \end{bmatrix},$$

where a and b denote the same point before and after reflection, respectively.

In our assumption, the axes are not aligned, however, so the reflection matrix must be replaced with the result of $T(-\theta_t)R(r_x,r_y)T(\theta_t)$, where $T(\theta)$ is the rotation matrix:

$$\begin{bmatrix} \cos\theta & 0 & -\sin\theta & 0 \\ 0 & \cos\theta & 0 & -\sin\theta \\ \sin\theta & 0 & \cos\theta & 0 \\ 0 & \sin\theta & 0 & \cos\theta \end{bmatrix}.$$

Thus, the overall ray matrix for one cycle of the beam's propagation through the cell is:

$$C = D(d+\delta)T(-\theta_t)R(r_x,r_y)T(\theta_t)D(d+\delta)R(r_x,r_y),$$

and the location of the spot after N cycles is then found from:

$$\begin{bmatrix} x_N \\ x_N' \\ y_N \\ y_N' \end{bmatrix} = C^N \begin{bmatrix} 0 \\ 1 \\ 0 \\ 1 \end{bmatrix},$$

where we have assumed that the beam entered at $x=y=0$ with unit slopes.

With the aid of a computer, the values of $\theta_t''$ and $\delta''$ that make $(x_N^2+y_N^2)^{\frac{1}{2}}$ approach zero (to within a specified tolerance) can readily be found. Many optimization routines are appropriate for this purpose. The one that I have employed is an implementation of the Nelder-Mead simplex algorithm described in J. E. Dennis, Jr., and D. J. Woods, "Optimization on Microcomputers: The Nelder-Mead Simplex Algorithm," in *New Computing Environments: Microcomputers in Large-Scale Computing*, A. Wouk, ed., SIAM 1987, pp. 116–122. In practice, I start by using the routine to minimize $(x_N^2+y_N^2)^{\frac{1}{2}}$ for a relatively small value of e and then use the resultant $\theta_t''$ and $\delta''$ values as starting points in a minimization run with a slightly larger value of e. I repeat this process until I reach the desired e value. To find $\theta_t''$ and $\delta''$ values for an e value of 0.005, for instance, I might first find them for an e value of 0.001 and then proceed to 0.005 in steps of 0.001.

When this is done, the spot coordinates, as a function of their order of occurrence, still show only frequencies of $k_x/N$ and $k_y/N$ cycles/spot, each of which has an associated axis along which the spot coordinates show no variation at the other frequency. These axes will be called here the high-frequency and low-frequency axes, respectively. As e increases from zero:

(a) the axes associated with the two spot frequencies rotate out of coincidence with the x and y axes;

(b) the amplitude of spot motion along one spot axis decreases, while along the other it increases; and (c) the angle between the two axes changes from 90°.

Unlike conventional astigmatic off-axis cavity absorption cells, those of the present invention will ordinarily end up with significant twist angles. Even with a tolerance of only 0.001%, the design-center twist angle is typically about 3.5°, so the twist angle of the actual resultant cell would ordinarly be greater than about 1°. As a practical matter, moreover, one will not ordinarily require a tolerance less than 0.1% if it can be avoided, and this corresponds to a design-center twist angle that exceeds 10°.

Regardless of whether this initial position is employed, the separation and twist angle are adjusted, as was mentioned above, to achieve the desired path. By shining a visible-light beam in at the proper entrance angle and placing a white card, for instance, in line with the exit aperture at proper exit angle, one can determine which way the final spot needs to be adjusted if at least some light from the Nth traverse initially leaves the aperture. If not, those with experience in similar aligning procedures can alternatively observe the pattern made on one of the mirrors by scattered light from the first few spots and then adjust them toward the calculated pattern. This serves to move the final spot to the aperture, after which any further alignment can be made by reference to the exit spot.

This adjustment process is considerably more straightforward than the requirement for a two-parameter adjustment might at first make it appear. In fact, the results of each parameter's adjustment are largely independent, as will be explained below in connection with FIG. 6. Before turning to FIG. 6, however, we will first discuss two example arrangements, which are particularly advantageous.

Figure 4:
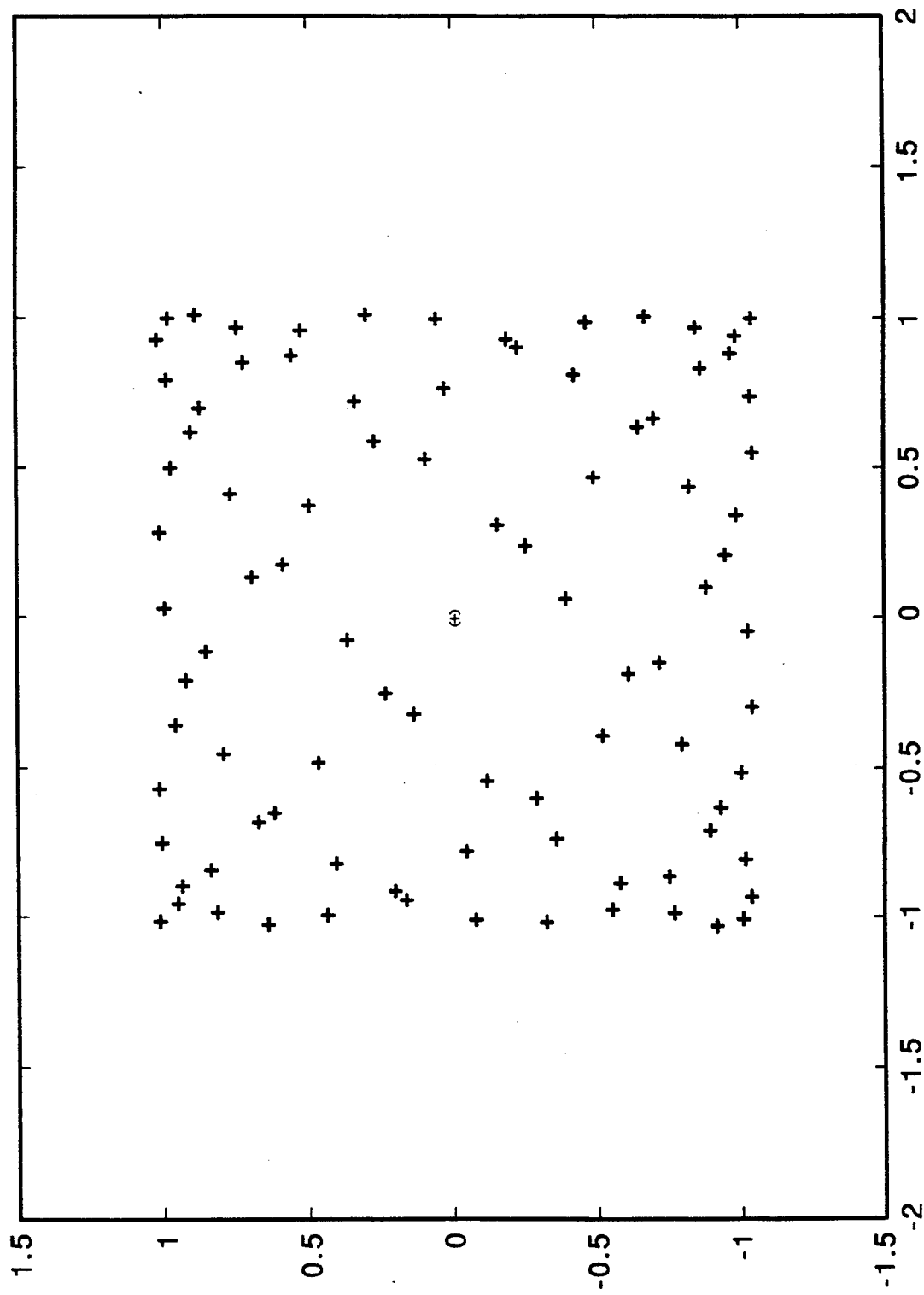
FIG. 4 is a diagram of the positions at which the light beam hits a mirror in a particularly advantageous prototype cell arrangement.

Any prototype cell having the relationships described above among $k_x$, $k_y$, and N would achieve the desired result: its light beam leaves the cell at the end of N cycles. However, not all such patterns are equally desirable in a practical absorption cell, and FIG. 4 depicts the pattern that results from a particularly desirable configuration.

Note that a single spot is positioned at the origin. This represents the exit position. Because of the unavoidably finite sizes of the light spots, at least a minimum separation must be provided between the exit position, i.e., the center of the Nth spot, and the center of the spot closest to it if spillover from that spot is to be avoided. It is therefore a desirable feature of a spot pattern that, aside from the exit spot, the ratio that the distance to the closest spot bears to that of the farthest spot should be relatively high, as it is in FIG. 4; the smallest cell diameter for a given beam size results when this ratio is greatest.

Another feature, not apparent in the drawing, is that the cell is close to confocal; that is, the radii of curvature are near in value to the mirror separation. This is desirable because it keeps the spot diameters for a Gaussian laser beam low and thus minimizes overall cell size. Practical parameter limits that fulfill this requirement are $0.35 < k_x/N < 0.65$ and $0.35 < k_y/N < 0.65$.

Finally, the spots corresponding to the high value of n (except for n=N itself) should not be among those closest to the origin, because spillover of light from spots close to the coupling hole can cause interference fringes and thus spurious modulation of the transmitted light, and these fringes are most difficult to remove when they result from light that spills over at the end of a partial path whose length is similar to that of the complete path. As it turns out, this means that the closest spots should occur for $n \approx N/2$, because, for every spot corresponding to a low value of n, there is a symmetrically placed spot corresponding to a high value of n. This, incidentally, is the reason why weakly astigmatic cells of the type described in Herriott et al. II are not particularly desirable; some of their closest spots occur at high values of n. The method of the present invention makes it more practical to use more-strongly astigmatic mirrors.

I have found two particularly favorable prototype cells, which I will refer to as cell I and cell II. In cell I, $k_x=40$, $k_y=38$, and N=91, while $k_x=86$, $k_y=81$, and N=185 for cell II. FIG. 4 depicts the pattern of cell I.

Figure 5:
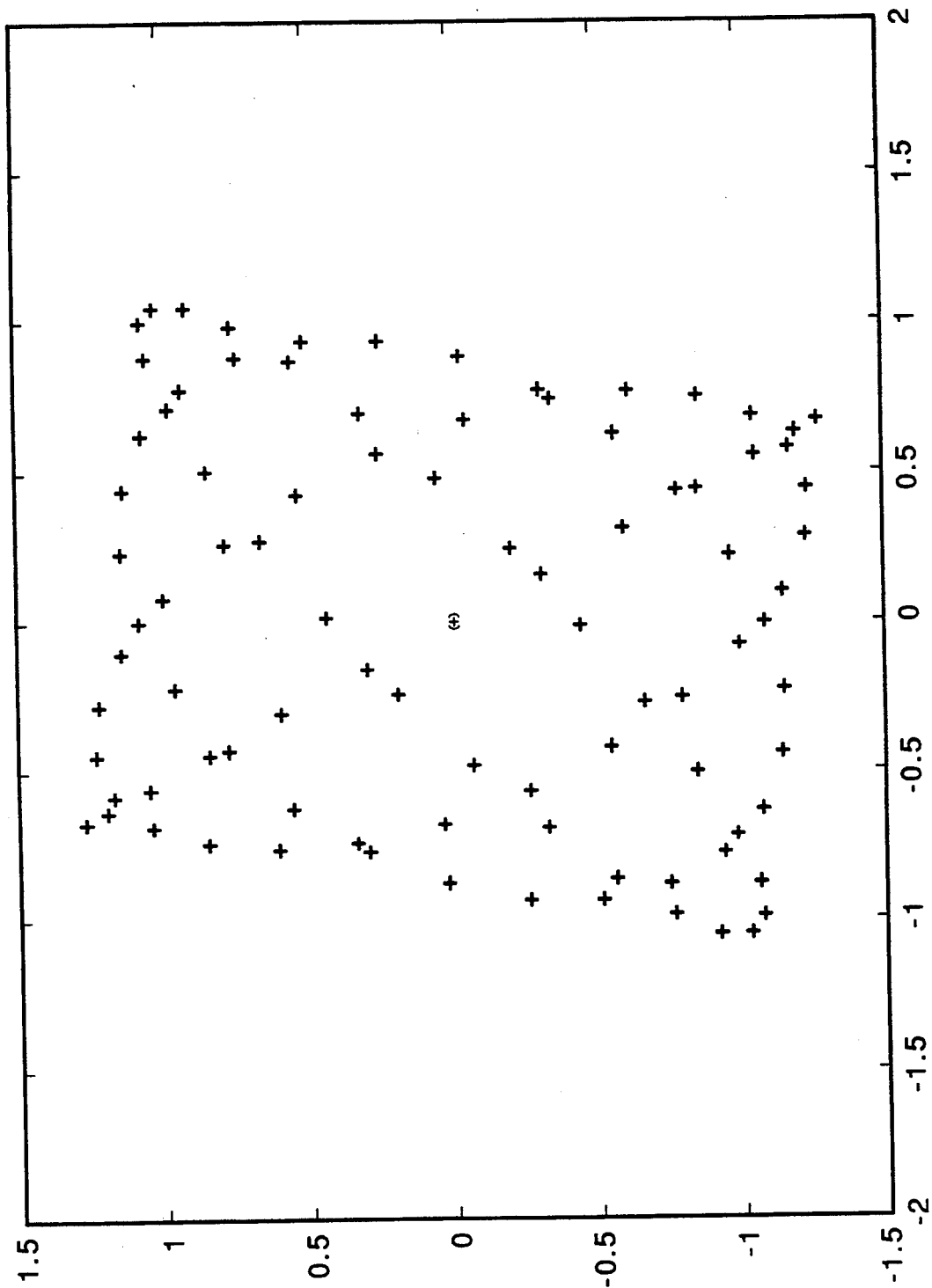
FIG. 5 is a similar diagram of the pattern that results when the prototype cell values are modified to design-center values that permit adjustments to be made in accordance with the present invention.

Rather than specifying mirrors with nominal curvature-radius values that would produce this prototype-cell pattern, however, the mirrors are specified to have radii adjusted from these values in accordance with expected manufacturing tolerances, as was explained above. With these adjusted nominal values, it is necessary to employ a twist angle and a separation offset to get the Nth spot to hit the center of the exit aperture. If it is assumed that the radii can be achieved to within a tolerance of 0.2%—i.e., if e=0.002—and the desired path length is 100 (the distance units here being arbitrary), then the cell-I prototype values are $r_x=0.67728$, $r_y=0.73854$, and d=0.54945, while the design-center values based on this prototype are $r_x''=0.67323$ and $r_y''=0.74151$. For this arrangement, the required values of twist angle and separation offset are $\theta_t''=-17.02°$ and $\delta''/d=-3.93 \times 10^{-4}$; i.e., $d+\delta''=0.54923$. FIG. 5 depicts the pattern that results from the design-center values based on cell I.

In accordance with the tolerance assumption, the radii will not in general equal these nominal values exactly, so the thus-calculated values of twist angle and separation offset will not in general result in the beam's hitting the center of the exit aperature at the end of the Nth cycle. However, adjustment to achieve this result is fairly simple, as can be appreciated by reference to FIG. 6.

Figure 6:
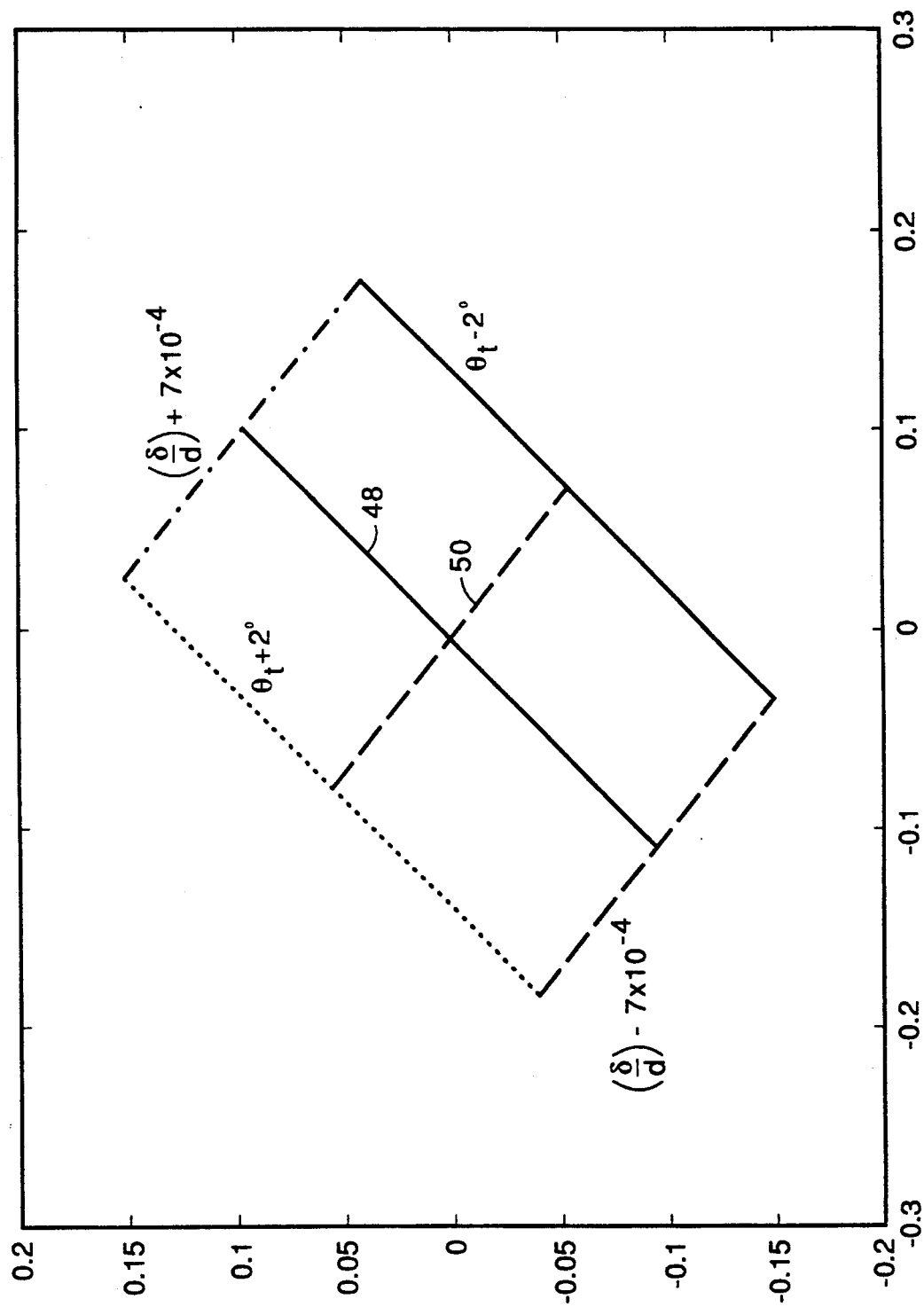
FIG. 6 is a diagram containing the loci of exit points that result from adjusting a cell made in accordance with the teachings of the present invention.

FIG. 6 is a graph of Nth-spot-position loci for various ranges of the values for $\theta_t$ and $\delta/d$. That is, the calculation of the FIG. 6 values are based on the assumption that the curvature radii are precisely the design-center values, and FIG. 6 shows what happens when the twist angle is varied from the nominal value $\theta_t''$ described above and the separation is varied from the nominal value $d+\delta''$ described above. But other curvature-radius values within the tolerance range would result in plots similar in shape, although centered on a different location.

In FIG. 6, locus 48 depicts the value of the Nth spot as the twist angle remains $\theta_t''$ but the normalized offset from the prototype separation d is varied between a value of $(\delta''/d)-7\times 10^{-4}$ through $(\delta''/d)+7\times 10^{-4}$, while locus 50 represents the motion of that spot when the separation between the mirrors remains at the calculated value of $d+\delta''$ but the twist angle varies from $\theta_t''-2°$ through $\theta_t''+2°$. It is clear from FIG. 6 that the directions in which the spot moves in response to the two adjustments are largely independent of each other, so the adjustment is straightforward.

It is thus clear that the teachings of the present invention enable one to fabricate an off-axis cavity absorption cell that takes full advantage of the potential of the astigmatic-mirror principle without imposing excessively stringent manufacturing requirements and without requiring difficult-to-maintain mirror warping. The invention thus constitutes a significant advance in the art.

What is claimed is:

1. An absorption cell forming a coupling aperture and comprising opposed astigmatic mirrors that define an actual closed optical path from the coupling aperture and back to it, consisting of an odd number N of cycles through the absorption cell, in which the locations of the spots at which the actual path hits one of the mirrors, as a function of those spots' order of occurrence, exhibits motion consisting essentially of only two frequency components $k_x/N$ and $k_y/N$ associated with high-frequency and low-frequency axes, respectively, along which the contribution of the other frequency component is essentially zero, where $k_x$ and $k_y$ are different integers and their common factors, other than unity, with N are distinct, each of the mirrors having principal radii $r_x'$ and $r_y'$ related to the principal radii $r_x$ and $r_y > r_x$ of a prototype cell by the relationships $r_x' < r_x/(1+\Delta e)$ and $r_y' > r_y/(1-\Delta e)$, where $\Delta e = 2 \times 10^{-4}$, the axes of the prototype cell's mirrors are oriented with their principal axes aligned and define a prototype closed optical path consisting of the same odd number N of cycles through the prototype cell, and the locations at which the prototype path strikes a mirror make $k_x$ cycles in the direction of one principal axis and $k_y$ cycles in the direction of the other principal axis.

2. An absorption cell as defined in claim 1 wherein the actual path consists of 182 traverses between the mirrors, during which the position at which the light hits a mirror executes forty cycles along the high-frequency axis and thirty-eight cycles along the low-frequency axis.

3. An absorption cell as defined in claim 1 wherein the actual path consists of 370 traverses between the mirrors, during which the position at which the light hits a mirror executes eighty-six cycles along the high-frequency axis and eighty-one cycles along the low-frequency axis.

4. An absorption as defined in claim 1 wherein $0.35 < k_x N < 0.65$ and $0.35 < k_y N < 0.65$.

5. An absorption cell forming a coupling aperture and comprising opposed astigmatic mirrors forming a twist angle of more than 1.0 degree with respect to each other and defining, for light entering the coupling aperture at a predetermined angle, a closed multiple-reflection path from the inlet aperture and back to it.

6. An absorption cell as defined in claim 5 wherein each mirror's ratio of maximum to minimum radius of curvature exceeds 1.001.

7. An absorption cell as defined in claim 5 wherein the twist angle between the mirrors exceeds 10 degrees.

8. A method of constructing an absorption cell comprising the steps of:
   A) constructing a cell that forms a coupling aperture and includes opposed astigmatic mirrors spaced apart along a central axis therethrough; and
   B) varying the mirrors' twist angle and their separation along the central axis until, at a twist angle that exceeds 1.0 degree, the mirrors define, for light entering the inlet aperture at a predetermined angle, a closed multiple-reflection path from the coupling inlet aperture and back.

9. A method as defined in claim 8 wherein the step of varying the mirrors' twist angle comprises varying it to a value, at which the mirrors define the multiple-reflection path, that exceeds 10 degrees.

10. A method as defined in claim 9 wherein each mirror's ratio of maximum to minimum radius of curvature exceeds 1.001.

11. A method as defined in claim 8 wherein each mirror's ratio of maximum to minimum radius of curvature exceeds 1.001.

* * * * *